United States Patent [19]

Hiller

[11] E Re. 29,297

[45] Reissued July 12, 1977

[54] CHEMICAL CLOSETS

[76] Inventor: Montague Hiller, 20 Carrington Avenue, Borehamwood, Hertfordshire, England

[21] Appl. No.: 600,477

[22] Filed: July 30, 1975

Related U.S. Patent Documents

Reissue of:

[64] Patent No.: 3,748,663
Issued: July 31, 1973
Appl. No.: 121,839
Filed: Mar. 8, 1971

[51] Int. Cl.[2] ..... A47K 11/02; A61L 11/00

[52] U.S. Cl. ..... 4/115; 4/10; 4/85; 4/116

[58] Field of Search ..... 4/10, 1, 115, 77, 76, 4/78, 85, 90, 93, 116

[56] References Cited

U.S. PATENT DOCUMENTS

| | | | |
|---|---|---|---|
| 2,224,868 | 12/1940 | Houck et al. | 4/115 |
| 3,289,214 | 12/1966 | Corliss | 4/115 |
| 3,418,664 | 12/1968 | Carmichael et al. | 4/115 |
| 3,557,388 | 1/1971 | Bach | 4/10 |
| 3,609,772 | 10/1971 | Howard | 4/115 |
| 3,611,446 | 10/1971 | Howard | 4/10 |
| 3,611,447 | 10/1971 | Howard | 4/10 |

*Primary Examiner*—Henry K. Artis

[57] ABSTRACT

A flushing unit for a chemical closet comprises a reservoir for flushing fluid and means for circulation of flushing fluid between the reservoir and a lavatory pan or bowl of a chemical closet. Provision is made so that the return conduit from the lavatory pan to the reservoir will not admit at any time solid material deposited in the lavatory pan. Passage of liquid deposited in the lavatory pan therefrom to the reservoir is generally prevented by ensuring that the return conduit is incapable of allowing the free flow therethrough of liquid except during transfer of flushing fluid to the lavatory pan or chamber. The return conduit can take the form either of a narrow bore tube through which liquid can only be passed under suction, or can be of wider bore having a suitable valve therein.

12 Claims, 5 Drawing Figures

CHEMICAL CLOSETS

Matter enclosed in heavy brackets [ ] appears in the original patent but forms no part of this reissue specification; matter printed in italics indicates the additions made by reissue.

This invention relates to chemical closets.

Transportable chemical closets which comprise a lavatory pan or bowl, the lower part of which can communicate with a container for a chemical solution, are already known. Since a piped supply of water is not generally available to effect flushing of the lavatory pan, recirculating units have been devised which, when the contents of the lavatory pan have passed into the lower part of the container, draw fluid from the container, wash it around the lavatory pan to remove adhering waste material therefrom and return it to the container or reservoir. A disadvantage of such an arrangement is that the fluid being recirculated gradually becomes more and more contaminated, carrying an increasing amount of solids in suspension, so that a stage is reached at which the fluid being recirculated tends to foul the lavatory pan rather than flush it clean.

It is an object of the invention to provide a transportable chemical closet which is more sanitary and hygenic then similar apparatus hitherto generally in use and wherein the flushing thereof will be greatly facilitated.

[According to one aspect of the present invention, there is provided a flushing unit for a transportable chemical closet comprising, in combination, a reservoir for a flushing fluid, means for delivery of fluid from the reservoir to the lavatory pan or bowl of the closet to effect flushing thereof and conduit means to the reservoir to enable, in use, flushing fluid to be returned from the lower part of the lavatory pan or bowl to the reservoir, which conduit means is so adapted that solid waste material deposited in the lavatory pan or bowl is unable to pass therethrough to the reservoir.]

According to [a second] *one* aspect of the invention, there is provided a transportable chemical closet comprising a casing adapted to provide a container for a chemical solution, a lavatory pan or bowl located within the casing at the upper part thereof and having a discharge aperture at its lower part, closure means for the discharge aperture and a flushing unit which comprises a reservoir for a flushing fluid, means for delivery of fluid from the reservoir to the lavatory pan or bowl of the closet to effect flushing thereof and conduit means to the reservoir to enable, in use, flushing fluid to be returned from the lower part of the lavatory pan or bowl to the reservoir, which conduit means is so adapted that solid waste material deposited in the lavatory pan or bowl is unable to pass therethrough to the reservoir.

*According to a second aspect of this invention, there is provided a sanitary closet comprising*

*a. a bowl portion having a bottom outlet,*

*b. a waste receptacle positioned below said bowl for receiving liquid and solid waste admitted to said bowl and passing through said bottom outlet,*

*c. closure means operable between open and closed positions for selectively permitting solid and liquid waste to pass from said bowl to said waste receptacle,*

*d. means defining a separate reservoir for flushing fluid, said reservoir being positioned above said bowl outlet and around said bowl portion,*

*e. sump means positioned below said bowl outlet and about said waste receptacle for collecting flushing fluid when said closure means is closed,*

*f. means defining a separate flow path for said flushing fluid from said bowl to said sump when said closure means is in a closed position, thereby by-passing said waste receptacle,*

*g. pump means for forcing said fluid from said reservoir to said bowl to flush said bowl, said means also defining a separate flow path to return said flushing fluid from said sump to said reservoir.*

The closure means serves the dual function of obviating the incidence of unpleasant sights and smells at all times other than when it is desired to transfer the contents of the lavatory pan or bowl to the chemical solution, while preventing loss of flushing fluid into the container when flushing of the lavatory pan or bowl is being effected. The closure means can, for example, take the form described in British Pat. No. 1,034,650, and comprise a spring or weight loaded flap carried by a shaft which extends transversely of the container and which is supported for angular movement about its longitudinal axis. An actuating lever or handle is disposed externally of the casing so that appropriate angular movement can be imparted to the shaft to move the flap into an open position such that discharge of matter from the pan or bowl into the container can take place.

The flushing unit *of the closet* of the present invention *is generally located at a position around the lavatory pan or bowl and* will be operated after the contents of the lavatory pan or bowl have passed therefrom, generally to a container of the aforesaid type containing a chemical solution. The conduit to the reservoir for the flushing fluid from the lavatory pan or bowl must be so designed that solid material deposited in the lavatory pan, in particular faeces, will not be able to enter thereinto during use of the chemical closet. Hence, if as according to one embodiment of the present invention, the conduit has a relatively wide bore, a valve can be provided therein which is only opened when flushing is to be carried out, at which time the closure means will be kept closed. In such a case, operation of the means for delivery of the flushing fluid from the reservoir, the means generally being a pump, and operation of the valve means are advantageously synchronised with respect to one another so that the valve is only in the open position during operation of the delivery means, so that waste material, and in particular solid material, cannot ever escape into the reservoir. Furthermore, in such a case operation of the delivery means preferably can only take place when the valve is open so that overfilling of the lavatory pan or bowl cannot occur.

According to a further embodiment of the present invention, the use of a valve to prevent entry of waste material into the reservoir for flushing fluid can be dispensed with if the conduit means has such a narrow bore that only liquid can pass therethrough and entry of liquid thereinto is only possible when suction is applied to the end of the conduit means remote from the lavatory pan or bowl.

Since with a narrow bore conduit, there will be a tendency for a relatively large proportion of flushing fluid to be lost from the lavatory pan or bowl by seepage around the closure means, in comparison to the amount which enters the conduit means, it is proposed that when the flap or other closure means is in place, sealing of the discharge aperture should be achieved by rubber or other elastomeric sealing means. Such sealing means can take the form of a membrane in which case the closure flap can be dispensed with if the membrane is sufficiently strong to serve as a base portion of the lavatory pan or bowl. If a closure flap is employed, the sealing membrane will both close the discharge aperture and provide a seal around the flap in the region of the perimeter of the discharge aperture. Such a sealing membrane is generally disposed around a ring preferably of U-shaped section *constituting a small sump positioned below the bowl outlet* so that when the ring is forced into the discharge aperture by the closure flap or other means acting on the sealing membrane arrangement, the discharge aperture will be sealed off from the chemical solution in the container below the lavatory pan or bowl.

The flushing fluid will generally contain an additive so that it will always be sterile. Such additive can for example be the same as the chemical component of the chemical solution in the container below the lavatory pan or bowl. The component members of the chemical closet, and in particular the sealing means should be made of a material which is resistant to attack by waste products deposited in the lavatory pan or bowl. In particular, the sealing means should be resistant to attack by ammonia.

In order that the invention may be clearly understood and readily carried into effect, reference will now be made, by way of example only, to the accompanying drawings in which.

Figure 1:
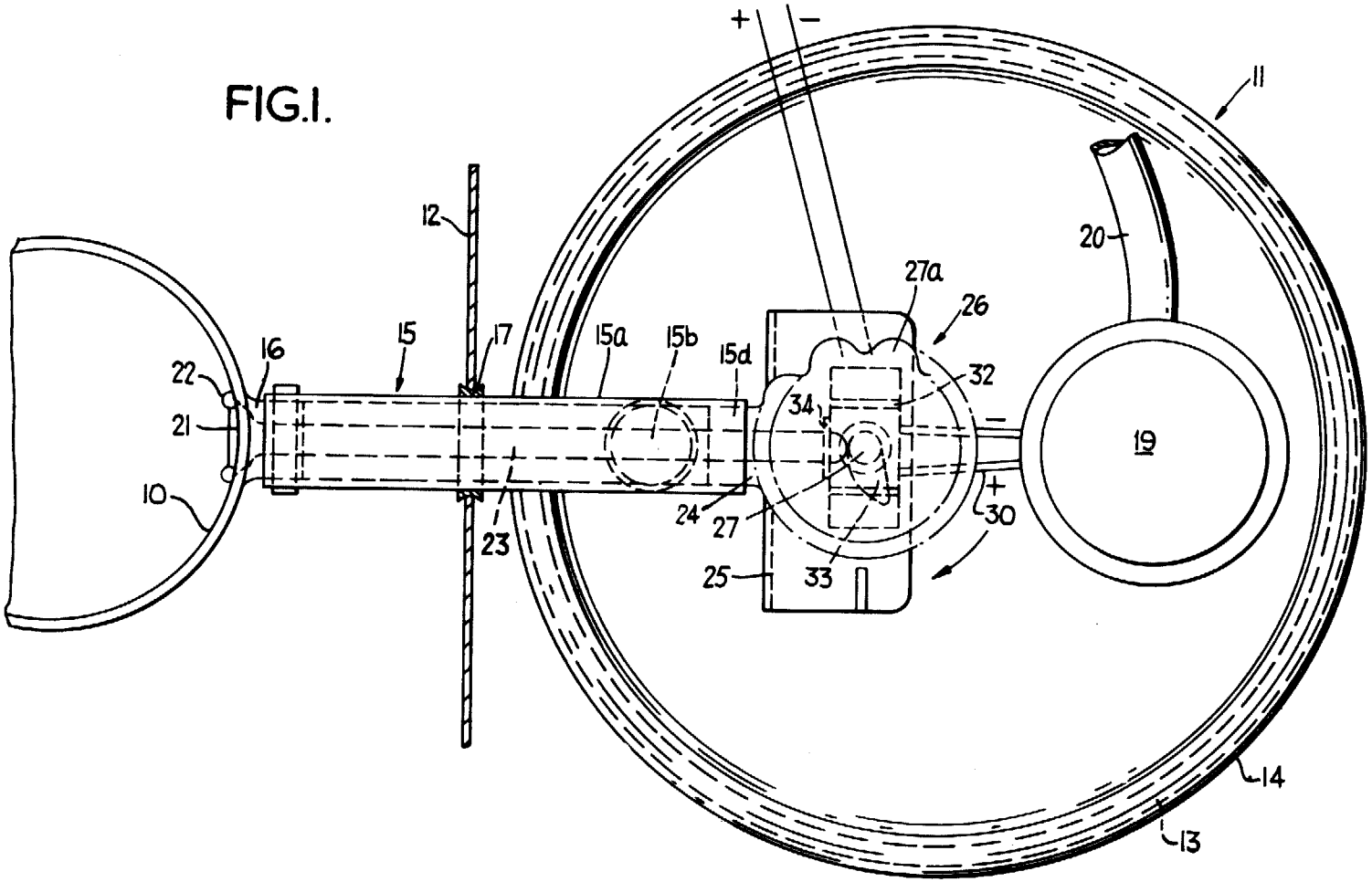
FIG. 1 is a diagrammatic plan view of one flushing arrangement [according to the present invention] for use with a chemical closet [;] *according to the present invention;*
Figure 2:
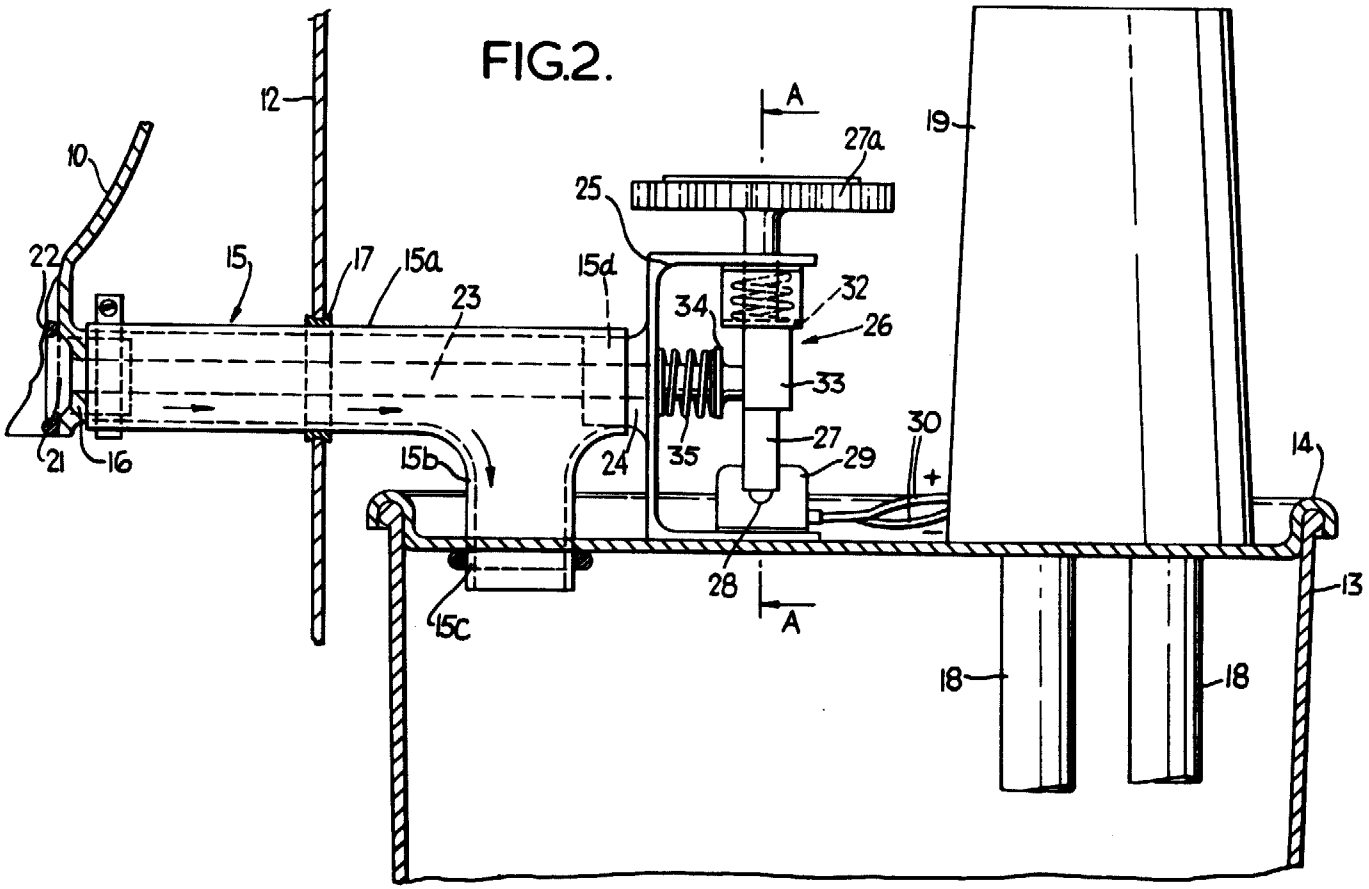
FIG. 2 is a diagrammatic longitudinal sectional view through the flushing arrangement shown in FIG. 1.
Figure 3:
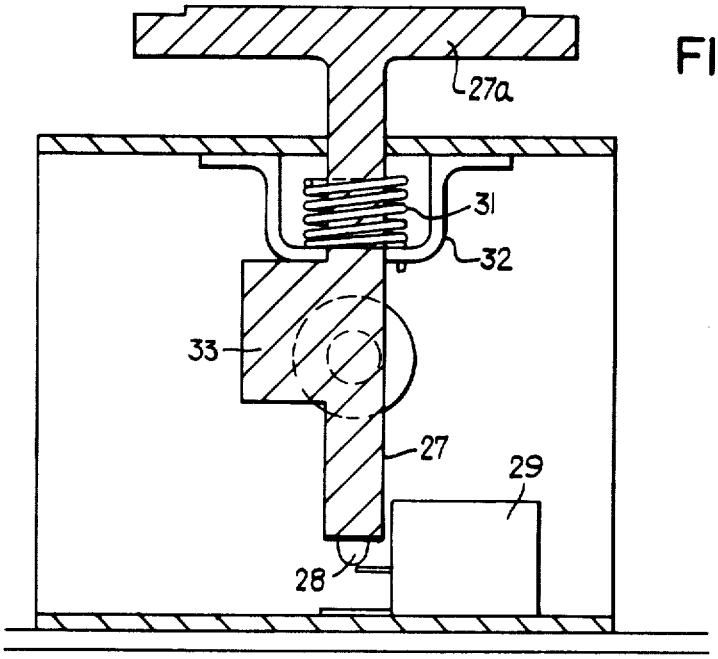
FIG. 3 is a section on the line A—A in FIG. 2.

Referring to FIGS. 1 to 3 of the drawings, 10 denotes a lavatory pan separated from a flushing unit denoted generally as 11 by a transverse partition 12 which divides an outer casing (not shown) into a forward compartment containing the lavatory pan 10 and a compartment which contains the flushing unit 11. The space in the forward compartment below the lavatory pan 10 will serve as a container for a chemical solution which is of such a nature as to sterilise and liquefy or cause emulsification of matter discharged thereinto. The solution employed will preferably consist of an admixture of chemicals in flake or other appropriate form, such chemicals being put into solution in an appropriate amount of water. An example of a suitable composition for this purpose is that which forms the subject of U.K. Pat. No. 1,114,808. A discharge aperture will generally be provided on the underside of the lavatory pan 10, normally being closed, but which can be opened when required to allow discharge of waste material into the chemical solution in the lower part of the forward compartment. The flushing unit 11 comprises a reservoir 13 which is provided with a cover member 14, both the reservoir 13 and the cover member 14 advantageously being made of a synthetic plastics material such as polyethylene in order that the rim of the reservoir may enter into snap-fitting engagement with the rim of the cover member in the manner shown in FIG. 2 of the drawings. An angled tube 15 which can also be formed of a synthetic plastics material joins a lower region of the lavatory pan 10 with the interior of the reservoir. One limb 15a of the tubular member 15 is mounted about an aperture 16 in the lower region of the lavatory pan 10, and passes through an aperture in the partition 12 in which it is held by a sealing member 17. A limb 15b of the tubular member 15, which lies within the rear compartment, is at right-angles to the limb 15a and enters into the reservoir 13 through the cover member 14, the hole in the cover member through which the limb 15b passes being sealed by a sealing ring 15c. The cover member 14 is also pierced by two supply ducts 18 to a pump 19 mounted on the upper surface of the cover member 14. The pump is provided with an outflow pipe 20 (FIG. 1) which can also be formed of a synthetic plastics material, for example polyethylene, and through which the contents of the reservoir can be passed to the lavatory pan or bowl to flush the same.

A valve plate 21 closes the aperture 16 in the lower region of the lavatory pan 10. A sealing ring 22 is provided around the circumference of the valve plate 21. The valve plate 21 mounts a rod 23 which is axially disposed in the limb 15a of the tubular member 15, in which it is displaceable to effect opening and closing of the aperture 16. The rod 23 passes through a side limb 15d of the tubular member 15, the side limb 15d being colinear with the limb 15d and engaging a tubular projection 24 mounted on a transverse wall of a casing 25 of a switch mechanism shown generally at 26. The rod 23 passes from the side limb 15d into the projection 24 and through the wall of the switch mechanism. The engagement of the side limb 15d and the tubular projection is such that fluid in the limb 15d cannot escape at the joint produced. Likewise, the fit of the rod 23 with a hole in the transverse wall of the casing 25 is such that fluid cannot enter the switch mechanism from the side limb 15d.

The switch mechanism consists of a vertically displaceable rod 27 which is provided with a knob 27a and which passes through the top of the casing 25. At the base of the rod 27 is a constant 28 which, when the knob 27a is fully depressed completes the circuit of a mercury switch 29 which can be connected to a car battery. The mercury switch 29 is connected to the motor of the pump 19 by wires 30. The rod 27, and hence the contact 28, is normally biased away from the mercury switch by means of a compression and torsion spring 31 which surrounds the rod in an upper region thereof, being housed in a compartment 32 in an upper region of the casing 25. About the middle of the rod 27 is mounted a cam 33 which is so disposed on the rod 27 that when the spring 31 holds the contact 28 apart from the terminals of the mercury switch 29, the projection of the cam will be level with, but at an angle to the axis of the rod 23 which projects into the housing 25. Within the confines of the casing 25, a plate 34 is mounted on the rod 23, being biased from the transverse wall of the casing 25 by a spring 35. The plate 34 is so disposed with respect to the cam 33 that rotation of the cam will cause the projection thereof to abut the reverse side of the plate 34 to that which contacts the rod 23, the reverse side of the plate 34 being shown in the drawing to be domed, and hence force the plate against the action of the spring 35 which will be compressed and hence cause axial displacement of the rod 23 in the limbs 15a and 15d of the tubular member 15 to open the aperture 16 in the lower part of the lavatory pan 10.

In order to operate the flushing unit 11, it is necessary to first ensure that the discharge aperture communicating the lower part of the lavatory pan 10 with the lower region of the forward compartment is closed. The knob 27a is then depressed so that the contact 28 completes the circuit of the mercury switch, and the pump 19 is then actuated, sterile fluid from the reservoir 13 being drawn through the supply ducts 18 by the pump which passes the sterile fluid through the outflow pipe 20 to the lavatory pan 10. In order to release sterile fluid which has entered the lavatory pan 10, the knob 27a should be given a turn sufficient to cause the cam 33 to abut the plate 34 and cause axial displacement of the rod 23 in the tubular member 15, thus opening the aperture 16. It is preferable that the opening of the aperture 16 be carried out simultaneously with actuation of the pump 19 in order to avoid overfilling of the lavatory pan 10 with sterile fluid. When flushing is complete, it is simply necessary to return the knob to its neutral position to stop operation of the pump. The torsion of the spring will cause the cam 33 to rotate and hence out of abutment with the plate 34, thus closing the aperture 16 against undesirable entry of waste material subsequently deposited in the lavatory pan 10.

Figure 4:
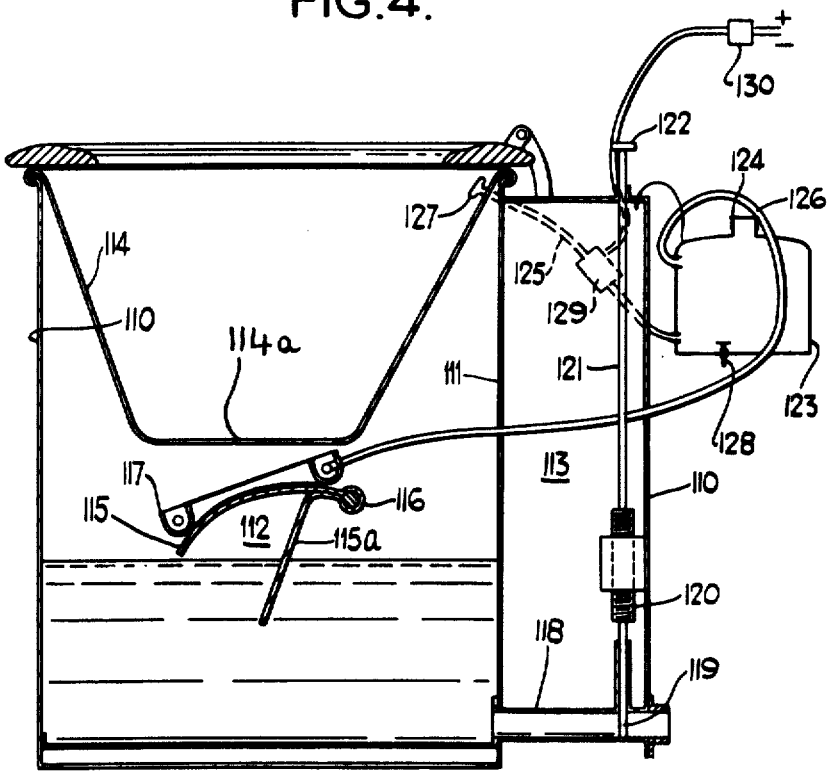
FIG. 4 is a diagrammatic sectional view of a chemical closet [embodying a second flushing arrangement] according to the invention [, and] *comprising a second flushing arrangement, and*

Referring next to FIG. 4 of the accompanying drawings, 110 denotes an outer casing which is appropriately shaped and dimensioned so that while suitable for the purpose in view it will also be completely stable when placed on a floor or other surface. The casing is divided by means of an internal transverse partition 111 into a relatively large forward compartment 112 and a smaller rear compartment 113. A lavatory pan or bowl 114 is located in the upper part of the forward compartment 112, the space in the latter below such pan being adapted to serve as a reservoir for a chemical solution of the type hitherto described for use in the forward compartment below the lavatory pan 10 of the chemical closet part of which is shown in FIGS. 1 to 3. The aforesaid pan 114 is provided at its lower part with a discharge aperture *114a* which is normally closed by means of a flap 115, the latter being disposed below the underside of the pan. The closure flap 115 which is conveniently of convex or part-spherical form as shown is carried by a shaft 116 the level of which in the casing 110 is below that of a sealing ring 117 of U-shaped section which carries a double membrane *and forms a small sump below the level of the bowl outlet or discharge aperture 114a*. The shaft 116 extends transversely of the forward compartment and is so supported as to be capable of angular or pivotal movement about its longitudinal axis. The sealing ring 117 is supported in the casing 110 so that it is free to move in a vertical direction towards and away from the lavatory pan or bowl 114. One end of the shaft 116 will project through a side wall of casing 110 and will be provided at such end with an actuating lever or handle (not shown), the arrangement being such that on appropriate operation of said lever or handle, the closure flap 115 will be moved from the open position shown to a position where, together with the sealing ring 117, it effectively closes the aperture in the pan 114. On actuation of the lever or handle in the opposite direction, the flap 115 and ring 117 will be removed from the vicinity of the aperture in the pan 114 so that any matter present in the pan will be discharged into the underlying reservoir under the action of gravity. The closure flap 115 will be appropriately loaded by means of a spring or weight so that upon release of the actuating lever, the flap will be restored automatically from the open position to the closed position.

At its lower part the partition 111 is provided with a discharge aperture, there being a discharge pipe 118 which leads from said aperture across the lower part of the rear compartment 113 and out through the rear wall of the latter. Disposed in the discharge pipe is a control valve for controlling the flow of effluent from the reservoir. Although various types of control valves can be employed, in the chemical closet illustrated, the control valve comprises a flat plate 119 which is so arranged as to be capable of sliding movement back and forth in a plane transverse to the discharge pipe 118 from a closed position where it will effectively prevent flow through the latter to an open position wherein flow will take place and vice versa. In the chemical closet illustrated, the plate 119 is attached to the lower end of a tube 120 which is internally screw-threaded.

Engaging in the screw-thread tube 120 is a threaded rod 121 which extends upwardly through a lid or cover at the top of the rear compartment 113. At its upper end the threaded rod 121 is conveniently provided with an actuating handle 122, the arrangement being such that rotation of the rod in one direction or the other will result in movement of the valve from its closed to its open position and vice versa.

In view of the possibility that the constituents of the chemical solution in the reservoir may tend to settle or separate out, it is advantageous to provide means for effecting periodical agitation of the contents of the reservoir. With that end view, a blade or paddle-like device 115a which is associated with the flap 115 extends into the reservoir for chemical solution, the arrangement being such that on each movement of the closure flap 115 the blade or paddle 115a will be effective to stir or agitate the contents of the said reservoir.

In order that the chemical closet should be flushed clean of any residual waste material, in particular solid material remaining on the internal wall of the lavatory pan 114, there is provided according to the present invention a flushing arrangement comprising a reservoir 123 which is *located at a position around the lavatory pan or bowl 114 and* provided with a closure member 124. The reservoir 123, the capacity of which can be from 2 to 4 imperial pints, should be mounted at a height at least equivalent to the height of the lavatory pan or bowl 114. Because of the relatively small size thereof, it can for convenience of access be simply *a separate container* hooked onto the outside of the casing 110 at any position about the perimeter thereof which is found to be convenient. Two orifices are provided in the wall of the reservoir 123 at different heights. Into the lower orifice is fitted a narrow bore polyethylene tube 125 which passes to one or more nozzles 127 mounted in an upper part of the wall of the lavatory pan 114. The upper orifice of the reservoir 123 is provided with a similar flexible narrow bore polyethylene tube 126 which passes through the casing 110 to the *sump-forming* groove of the U-shaped sealing ring 117 around which it is coiled. The part of the tube 126 which is coiled around the sealing ring 117 is provided with a number of holes in the wall thereof. A tap 128 is provided in the base of the reservoir 123 in order that liquid may be run off therefrom from time to time when it is desired to replenish the flushing liquid in the reservoir.

The flexible tube 125 leading to the nozzle(s) 127 is formed in two parts connected through a pump 129 which is connected through leads to a switch 130 which can be connected to a car battery. The switch 130 is advantageously of such a type that when depressed, it will remain in a depressed position for a fixed period of time sufficiently to achieve the desired flushing operation.

Figure 5:
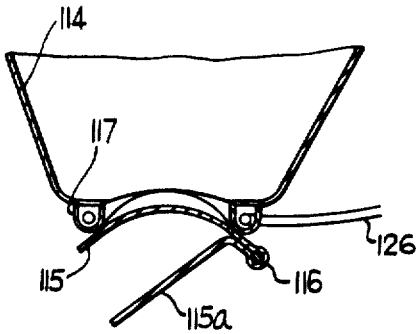
FIG. 5 is a diagrammatic sectional view of part of the chemical closet of FIG. 4 showing the arrangement of component members when the flushing arrangement is in use.

In order to operate the flushing arrangement shown in FIG. 4, it is first necessary to ensure that the discharge aperture communicating the lower part of the pan 114 with the lower region of the forward compartment is closed. The discharge aperture will then be sealed in the manner shown in FIG. 5. The switch 130 is then actuated and the pump 129 is set in motion so that water is withdrawn from the reservoir 123 and sprayed around the lavatory pan 114. The sprayed flushing fluid flushes the wall of the lavatory pan and descends to the region of the perforated part of the tube 126. Owing to the withdrawal of fluid from the reservoir 123, a vacuum is produced in the upper region thereof and as soon as the level of flushing fluid drops below the level of the upper orifice, flushing fluid in the lavatory pan can be withdrawn by suction through the tube 126 into the reservoir 123 where it replenishes the flushing fluid therein. In this way a continuous circulation of flushing fluid can be achieved for as long as desired. It is important that during such flushing operation a good seal is maintained in the region of the discharge aperture of the lavatory pan in order that seepage of flushing fluid should be reduced to the minimum. Likewise, the various apertures in the wall of the reservoir 123 should be air-tight. By the use of the narrow bore tube 126, it is impossible for fluid to pass therethrough unless under suction and therefore although the apertures will always be exposed to the contents of the lavatory pan, fluid will only pass therethrough during the flushing operation.

The flushing fluid employed in the flushing arrangements hitherto described will generally be made sterile by addition thereto of a chemical solution of a sterilising agent. The life of this sterile flushing fluid thus produced will be considerably longer than that of a sterile fluid containing discharged waste material hitherto used as flushing fluid. When it is considered that the flushing fluid in the reservoir therefor has become sufficiently contaminated to require its disposal, it is simply necessary to discharge the sterile fluid from the reservoir therefor in a suitable manner and refill the reservoir with fresh sterile fluid. In the embodiment shown in FIG. 4, it is not even necessary to remove the reservoir from the chemical closet for this purpose. A chemical solution of a sterilising agent can be added to the contents of the flushing fluid reservoir from time to time if desired.

A flushing arrangement such as indicated above will be sanitary and hygenic and as compared with flushing units for other chemical closets hitherto in use, the effectiveness of flushing will be greatly enhanced.

I claim:

1. A transportable chemical closet comprising a casing for containing a chemical solution in a lower region thereof, a lavatory pan or bowl located within said casing at an upper region thereof and having a discharge aperture at its lower part, closure means for said discharge aperture, said closure means being constrained to keep said discharge aperture closed at least when said pan or bowl is in use, and a flushing unit comprising a casing constituting a chamber for a flushing fluid, means defining an inlet passage to said chamber from a lower region of said pan or bowl, means defining an outlet passage to said pan or bowl from said chamber, means associated with said outlet passage for withdrawing the flushing fluid from said chamber through said outlet passage to said pan or bowl, said inlet passage being adapted so that solid waste material as is normally deposited in a lavatory pan or bowl cannot pass therethrough and so that liquid can only pass therethrough when said fluid withdrawing means is operating, when, with said closure means closed, the flushing fluid is circulated in a closed flow path which includes said pan or bowl and bypasses said lower region of the casing.

2. The transportable chemical closet as defined in claim 1, wherein said casing of the flushing unit has two apertures at different heights therein, first narrow-bore conduit means from the lower aperture defining said outlet passage and a further narrow-bore conduit means to the upper aperture defining said inlet passage, the bore of said further conduit means, at least in said lower region of the pan or bowl, being insufficient for liquid to enter thereinto other than when suction is applied to said further conduit means, said flushing unit further comprising nozzle means attached to said first conduit means at a location thereon within said pan or bowl.

3. The transportable chemical closet as defined in claim 2, further comprising sealing means for said discharge aperture, for sealing the latter when said closure means closes said discharge aperture.

4. The transportable chemical closet as defined in claim 1, wherein said means defining the inlet passage comprises a tube having a bore allowing the passage of liquid therethrough substantially only by suction produced at the other end thereof by withdrawal from said chamber of the flushing fluid through said means defining the outlet passage.

5. The transportable chemical closet as defined in claim 4, further comprising nozzle means intended for fixing to the inside wall of said pan or bowl, and narrow-bore tube means defining said outlet passage from said chamber to said nozzle means.

6. A transportable chemical closet as defined in claim 2, wherein said further conduit means extends within the interior of said pan or bowl in the region of said closure means, and is provided with a plurality of inlets communicating said further conduit means with said interior, which inlets are so dimensioned as to allow entry of liquid therethrough substantially only when suction is applied to said further conduit means.

7. A transportable chemical closet as defined in claim 4, wherein said tube extends within the interior of said pan or bowl in the region of said closure means, and is provided with a plurality of inlets communicating said tube with said interior, which inlets are so dimensioned as to allow entry of liquid therethrough substantially only when suction is applied to said tube.

8. The transportable chemical closet as defined in claim 1, wherein said means defining the inlet passage is provided with valve means for normally closing said inlet passage, and which is in operative association with said fluid withdrawing means whereby it can only be opened when said fluid withdrawing means is operating, and which valve means, when open, provides an entrance to said means defining the inlet passage, which is insufficient to allow passage therethrough of the solid waste material, but permits liquid to pass therethrough.

9. The transportable chemical closet as defined in claim 8, wherein said fluid withdrawing means is provided with means to render it operable only when said valve means is opened.

10. The transportable chemical closet as defined in claim 8, wherein said valve means comprises a cylindrical housing having an opening therein and constituting at least part of said inlet passage, a piston member reciprocably displaceable in said housing, to open and close said opening in dependence upon the position thereof, a cam member positioned to act on said piston member, further comprising means for rotating said cam member, and resilient biasing means against the action of which said piston member is displaced by said cam member.

11. The transportable chemical closet as defined in claim 8, wherein said fluid withdrawing means is provided with means to render it operable only when said valve means is opened, the latter comprising a cylindrical housing having an opening therein and constituting at least part of said inlet passage, a piston member reciprocably displaceable in said housing, to open and close said opening in dependence upon the position thereof, a cam member positioned to act on said piston member, and cause displacement of the latter, further comprising means for rotating said cam member, and resilient biasing means against the action of which said piston member is displaced by said cam member.

*12. A sanitary closet comprising*

*a. a bowl portion having a bottom outlet,*

*b. a waste receptacle positioned below said bowl for receiving liquid and solid waste admitted to said bowl and passing through said bottom outlet,*

*c. closure means operable between open and closed positions for selectively permitting solid and liquid waste to pass from said bowl to said waste receptacle,*

*d. means defining a separate reservoir for flushing fluid, said reservoir being positioned above said bowl outlet and around said bowl portion,*

*e. sump means positioned below said bowl outlet and about said waste receptacle for collecting flushing fluid when said closure means is closed,*

*f. means defining a separate flow path for said flushing fluid from said bowl to said sump when said closure means is in a closed position, thereby bypassing said waste receptacle,*

*g. pump means for forcing said fluid from said reservoir to said bowl to flush said bowl, said means also defining a separate flow path to return said flushing fluid from said sump to said reservoir.*

* * * * *